United States Patent [19]

Swank

[11] 3,965,896
[45] June 29, 1976

[54] BLOOD AUTOTRANSFUSION METHOD AND APPARATUS

[76] Inventor: Roy L. Swank, 4400 SW. Scholls Ferry Road, Portland, Oreg. 97225

[22] Filed: June 17, 1974

[21] Appl. No.: 479,764

[52] U.S. Cl. ............................. 128/214 R; 128/276
[51] Int. Cl.² ..................... A61M 5/14; A61M 1/02
[58] Field of Search ......... 128/214 R, 214 B, 214.2, 128/276, 277, 278

[56] References Cited
UNITED STATES PATENTS

| | | | |
|---|---|---|---|
| 2,804,075 | 8/1957 | Borden | 128/277 |
| 3,191,600 | 6/1965 | Everett | 128/276 |
| 3,492,991 | 2/1970 | Dyer | 128/214 R |
| 3,610,226 | 10/1971 | Albisser | 128/214 R X |
| 3,770,129 | 11/1973 | Brumfield et al. | 128/214 R |
| 3,785,380 | 1/1974 | Brumfield | 128/276 |
| 3,807,401 | 4/1974 | Riggle et al. | 128/277 |

OTHER PUBLICATIONS

Riggle et al. — Amer. Jour. Surgery, vol. 123, Mar., 1972, pp. 257–260.

Primary Examiner—Dalton L. Truluck
Attorney, Agent, or Firm—Eugene D. Farley

[57] ABSTRACT

Blood is autotransfused during surgical procedures involving a bleeding wound in which blood accumulates in the wound, by intermittently sucking the blood from the wound, anticoagulating the blood as it is collected, filtering the collected blood for the removal of debris and trauma-altered constituents and, during the course of the surgical procedure, returning the blood to the circulatory system of the same patient from whom it was collected.

9 Claims, 6 Drawing Figures

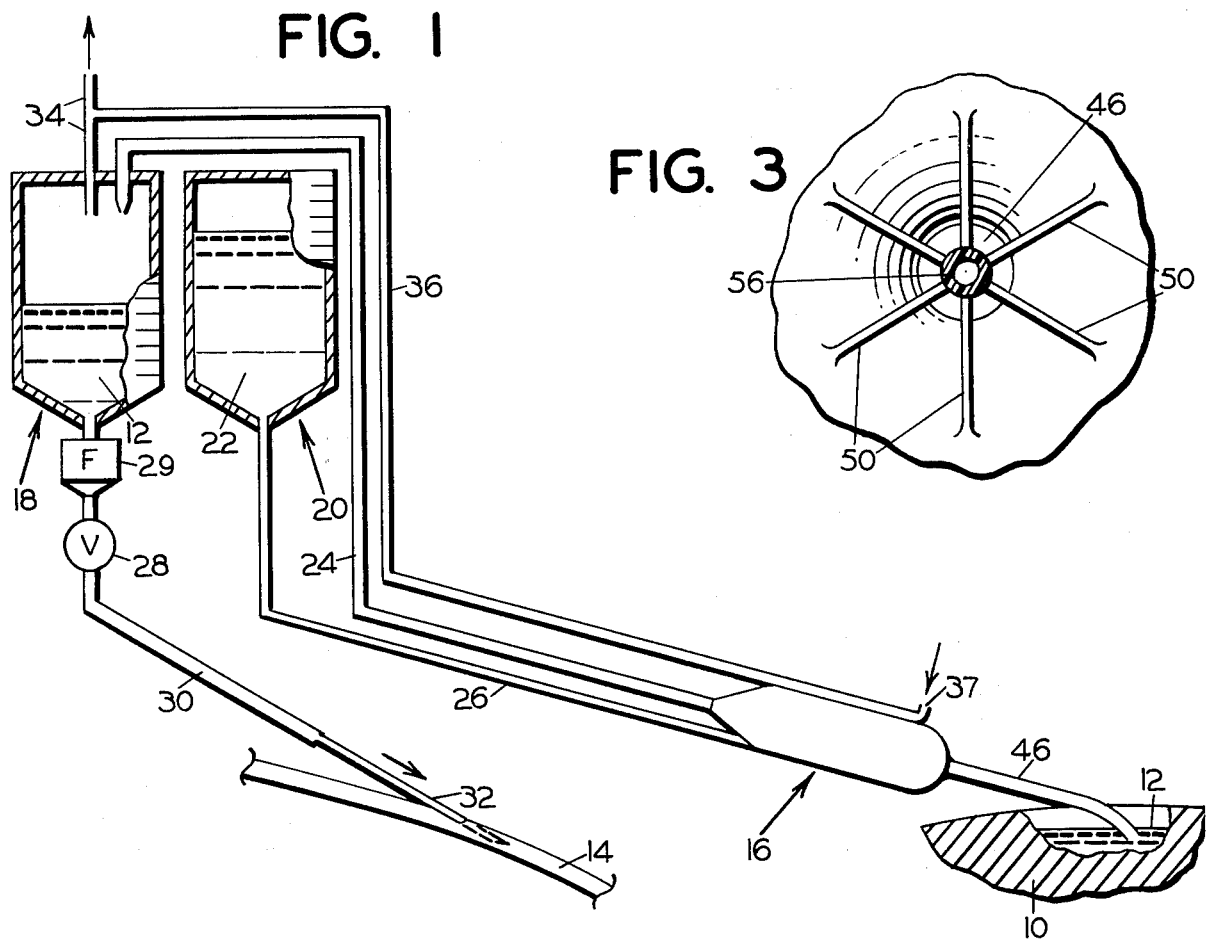
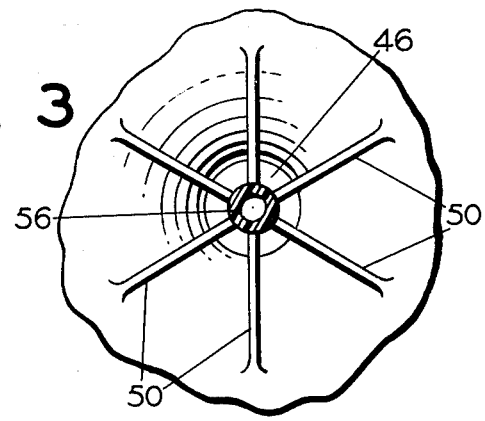
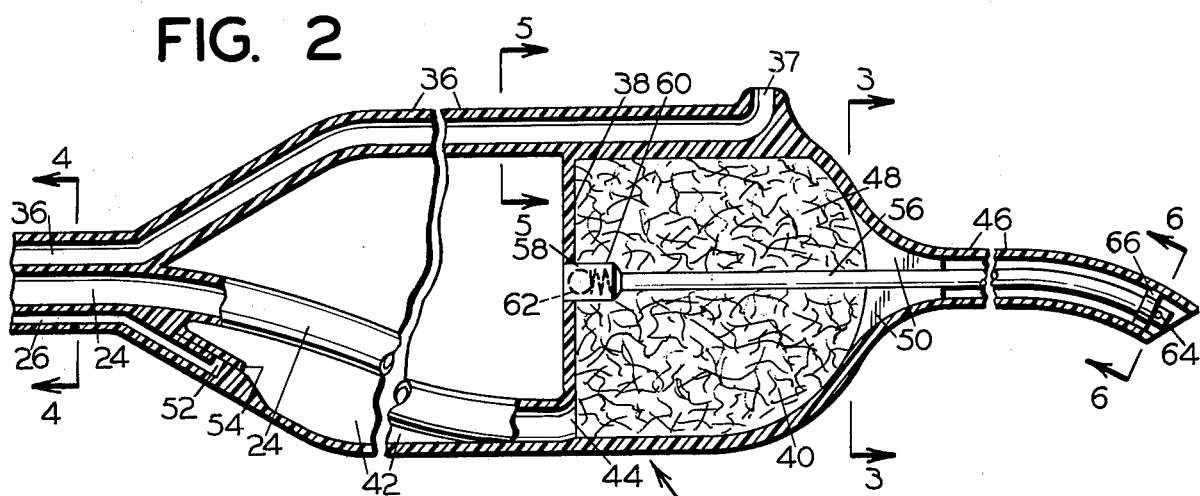
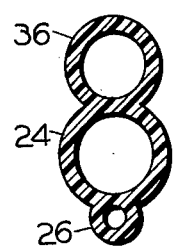
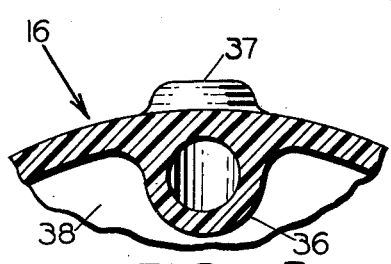
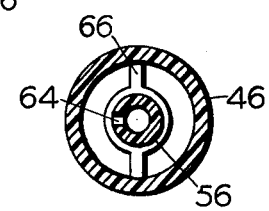

BLOOD AUTOTRANSFUSION METHOD AND APPARATUS

BACKGROUND OF THE INVENTION

This invention relates to the autotransfusion of blood during surgical procedures.

By the autotransfusion of blood is meant collecting blood from a bleeding wound and transfusing it into the circulatory system of the same patient from whom it was removed.

Suitable apparatus and techniques for carrying out autotransfusions presently are not available for application in routine surgery. As a consequence, it is conventional practice for the surgeon or his assistants to soak up the blood in the wound with surgical sponges which thereafter are discarded. The sponges are counted before and after each operation, to insure against one being left and subsequently sewn up in the wound.

This procedure has obvious and significant disadvantages. It wastes the patient's blood. It requires typing the patient's blood. In many cases transfusions are necessary, requiring drawing on the hospital's supply of blood bank blood. This not only depletes the hospital's store of blood, but also adds an additional element of cost to the operation. Furthermore, in transfusions involving blood bank blood there is always the danger of detrimental reaction caused by mismatching of blood types or other factors.

Also, present procedures place an added responsibility on the surgeon and his staff in that they are required to handle and keep track of the sponges applied to the wound.

Although autotransfusing the patient's own blood during the course of a surgical operation would provide a solution to the foregoing problems, this technique presently is not practiced widely because of serious inherent difficulties.

The patient's blood tends to clot as soon as it is withdrawn from the body and in its clotted form is not suitable for autotransfusion. It is difficult to control the clotting by the addition of heparin or other anti-clotting agents because the blood is to be reintroduced into the same patient from whom it was withdrawn. If too little heparin is added, the blood will clot. If too much heparin is added, the entire blood content of his body will be anti-coagulated so that the wound will not stop bleeding.

Furthermore, it is difficult to meter both the correct amount of anticoagulant added to the blood as it is withdrawn from the wound, and the anticoagulant-treated blood returned to the patient's circulatory system, with sufficient precision to make the autotransfusion procedure of practical application.

Still further, it is difficult to remove the blood from the wound without drying it out, or foaming it, or otherwise altering it so that it becomes unsuitable for reintroduction into the blood stream of the patient.

It accordingly is the general object of the present invention to provide method and apparatus for autotransfusing blood which overcomes the foregoing problems and provides a means for autotransfusing blood routinely during surgical operations, safely, with accurate control, without damaging the blood, and without requiring the use of highly skilled personnel or complicated and expensive equipment.

It is another object of the invention to provide blood autotransfusing apparatus in a form which may be sold commercially in aseptic condition at a cost so low as to make it economically possible to use the apparatus a single time only, as a disposable item.

THE DRAWINGS

In the drawings:

FIG. 1 is a view in elevation, partly in section, illustrating the hereindescribed blood autotransfusion apparatus illustrated in its application to the autotransfusion of blood during a surgical operation.

FIG. 2 is an enlarged view in longitudinal section of a combination blood collecting and anticoagulant dispensing subassembly employed in the apparatus of FIG. 1, and FIGS. 3, 4, 5 and 6 are detailed, transverse sectional views taken along lines 3—3, 4—4, 5—5 and 6—6 respectively of FIG. 2.

GENERAL DESCRIPTION OF THE INVENTION

Broadly considered, my invention comprises method and apparatus for the autotransfusion of blood during surgical procedures involving a bleeding wound in which blood accumulates in the wound.

The method essentially comprises the steps of intermittently sucking the blood from the wound during the surgical procedure, anticoagulating the blood as it is collected, filtering the collected blood for the removal of clots and other altered blood components, and returning the blood to the circulatory system of the same patient from whom it was collected.

The apparatus of the invention essentially comprises means for effectuating the above outlined method steps. Thus it comprises conduit means adapted to interconnect the wound and the blood circulatory member of the patient, an intermittently operated blood collecting unit in the conduit means, means for introducing anticoagulant in the collected blood, a blood filter in the conduit means downstream from the blood collecting unit, and a blood recycling unit in the conduit means downstream from the blood filter means.

The blood filter filters the collected blood for the removal of clots and other blood components which have been altered by trauma or exposure of the blood to physical agents present outside the patient's body. The blood recycling unit transfers the filtered blood back to the circulatory system of the patient from whom it was withdrawn.

In a preferred embodiment, the blood collecting unit comprises a suction unit which may be applied intermittently to the collection of the blood as it accumulates in the wound.

DESCRIPTION OF A PREFERRED EMBODIMENT

As illustrated somewhat schematically in FIG. 1, the herein described autotransfusion apparatus is employed in surgical situations in which a bleeding open wound is present in the body 10 of a patient. A quantity of blood 12 collects in the wound. This blood conventionally is absorbed in sponges and discarded. The apparatus of the invention functions to collect the blood and recirculate it to a vein 14 of the same patient from whom the blood was withdrawn.

The apparatus includes conduit means interconnecting the wound, which serves as a sump in which the blood developed by the operation accumulates, and the patient's vein, into which the collected blood is reintroduced. The conduit system includes a combination blood pump-anticoagulant dispenser-blood filter subassembly indicated generally at 16. It further includes a reservoir indicated generally at 18 for holding treated and filtered blood removed from the patient pending its recycling to his own circulatory system, and a storage vessel indicated generally at 20 for containing a quantity of heparin or other blood anti-coagulant solution 22. Reservoir 18 and storage vessel 20 are both closed, to insure sterility, but provided with suitable vents for admitting air as required for dispensing their fluid contents.

The foregoing three principal components of the apparatus are interconnected by suitable conduits which in the preferred embodiment of the invention comprise flexible, sterile plastic tubing. Thus the blood pumping-heparinizing-filtering sub-assembly 16 is connected to blood storage reservoir 18 by means of conduit 24. It additionally is connected to the anticoagulant storage vessel 20 by means of conduit 26.

Blood storage reservoir 18 communicates through a combination on-off check valve 28, and filter 29 with a third conduit 30. The latter terminates in a needle 32 which may be inserted in the usual manner into the vein 14 of the patient.

Blood reservoir 18 further is provided with a pipe 34 with communicates with a source of vacuum, for example a roller pump or the house vacuum line present in all hospital operating rooms. Pipe 34 connects with a by-pass line 36 through a T-connection. The by-pass line extends to, and is associated with, the combination blood collecting-heparinizing-filtering subassembly 16. It terminates in a finger closure 37 on the latter.

The entire assembly is mounted and arranged in the operating area, adjacent the table on which the patient lies. Blood reservoir 18 and anticoagulant supply vessel 20 are connected to suitable pumping means or mounted at an elevation for gravitational feed of their contents. Element 16 is dimensioned to be held by the surgeon or an operating assistant in such a manner that it may be used to collect the blood, introduce heparin or other anticoagulant into it, filter it, and transfer it into reservoir 18 from which it may be returned through check valve 28, through conduit 30 and back into the circulatory system of the same patient from whom it was withdrawn.

The construction and manner of operation of element 16 of the assembly are illustrated particularly in FIG. 2.

This key component of the hereindescribed apparatus preferably comprises a bulb made integrally of a suitable inert and non-toxic plastic and dimensioned to be held in the hand of an operator.

As illustrated, unit 16 comprises an outer case divided by partition 38 into a forward chamber 40 and a rearward chamber 42. The side walls defining chamber 40 preferably are relatively thick and rigid.

Forward chamber 40 is associated with the pumping function of the unit, used for collecting the blood which has accumulated in the wound. To this end it communicates through a port 44 in partition 38 with tube 24 which leads to and discharges into reservoir 18.

The forward portion of chamber 40 connects with a tube 46 which in effect is an extension of tube 24 leading to the source of vacuum.

Tube 46 has a length and contour suited for its intended purpose, viz. insertion into a pool of blood 12 inside wound 10 with the object in view of sucking the blood from the wound and transferring it into chamber 40 and thence into reservoir 12.

It is well known that blood withdrawn from a patient is altered rapidly by exposure to air, change in temperature, and factors associated with the trauma to which the patient is subjected. The change is evidenced in several ways.

First the blood is subject to incipient clotting. Second, its leucocyte and platelet components are altered. This alteration is evidenced by the fact that a proportion of the platelets become adhesive in character. Third, a proportion of the platelets form aggregates with a proportion of the leucocytes.

These altered components of the blood, as well as any extraneous debris which may be present must be removed if the blood is to be recycled to the patient, since if they are introduced into the patient's blood stream they will cause adverse reactions up to and including cessation of circulation.

Accordingly, chamber 40 is packed with a filter material 48 which has the capacity of removing these altered blood components, blood clots, and debris foreign to circulatory blood, without adversely affecting the patient's blood.

Such a filter material is described in my U.S. Pat. No. 3,448,041 METHOD AND APPARATUS FOR TREATING BLOOD PRELIMINARY TO ITS USE IN TRANSFUSIONS.

As set forth in the aforesaid patent, a filter material accomplishing the desired purpose comprises fibers or filaments of polyester resins (Dacron and Kodel), polyamide resin (Nylon), polyacrylic resin (Orlon), glass wool, steel wool, cotton, and cellulose (paper).

These materials are used in the forms of fibers or filaments having lengths of over 100 microns and diameters of less than 60 microns, preferably less than 30 microns. When blood containing altered components of the character described above is passed through a mat of such filamentous materials, the mat has the ability to extract selectively the altered blood components without adversely affecting the other constituents of the blood.

Accordingly, in the execution of the invention, chamber 40 is filled with packing of the foregoing or other suitable filter materials arranged in the chamber and spaced from the infeed end of blood collecting tube 46 by means of fins 50 in such a manner that blood sucked up through collection tube 46 passes through the filter enroute to reservoir 18.

Because of the inherent tendency of blood to clot, it is imperative for the successful use of the hereindescribed apparatus that a suitable blood anticoagulant such as heparin or acid-citrate-dextrose (ACD) solution be added to the blood as soon as possible after it leaves the circulatory system of the patient. The amount of blood anticoagulant added for this purpose must be carefully controlled within limits. If too little is added, coagulation occurs. If too much is added, and in view of the fact that the blood removed from the patient is to be returned to the patient's own blood stream, the patient may become "heparinized" with the result that his blood will not clot properly. This obviously interferes with proper healing of the operative wound.

It is a particular feature of the invention that means are provided for introducing heparin or other blood anti-coagulant to the blood both at the wound site as well as in the collecting apparatus. It is a further important feature that such means is subject to accurate control by the operator so that neither of the above undesirable contingencies occurs.

To this end, the side walls defining chamber 42, i.e. the blood anticoagulant containing chamber, are made flexible so that the device becomes an integral hand pump which may be operated intermittently by the exertion of squeezing pressure as required to dispense the desired amount of blood anticoagulant at selected time intervals, or whenever an accumulation of blood is present in the wound.

Thus a quantity of heparin or other blood anticoagulant solution is charged into reservoir 22 which communicates with chamber 42 via conduit 26 through port 52. A flapper valve 54 or other suitable type of valve may be placed in the conduit or port to prevent fluid flow in the reverse direction when squeezing pressure is applied to the side walls of the chamber.

At its upstream end, chamber 42 communicates with a discharge tube 56 through a port 58 in which is seated a spring pressed ball valve 62 or a suitable equivalent therefor. The latter valve functions to permit passage of the fluid in the outfeed direction only.

Conduit 56 which dispenses the heparin or other anticoagulant solution passes centrally and longitudinally through filter chamber 40, between fins 50 and out through spout 46 in which it is located substantially coaxially. It terminates in a head having laterally directed discharge ports 64 and supported in bracket 66. The head and discharge ports preferably are located at the discharge end of tube 46 so that the blood anticoagulant solution discharged through tube 56 is discharged both into the blood 12 contained in a pool in the wound, and into conduit 46 before it passes through filter material 48. This insures that the anticoagulant solution will be dispersed uniformly in all areas in which it is required.

OPERATION

The manner of operation of the hereindescribed apparatus for autotransfusing blood during surgical procedures involving a bleeding wound is as follows:

It is contemplated that multiple purpose unit 16 of the apparatus be supplied by the manufacturer as an integrally constructed unit, prepacked with fibrous filter material, packaged in sterile condition, and ready for use by the surgeon or his staff. Conduits 24, 26, 36 may be integral with unit 16 or supplied as connect-on tubes. Similarly, reservoirs 18, 20 may be integrated with the assembly as sterile plastic bags or supplied as separate elements to which the tubes are connected.

Using present day techniques for manufacturing plastic items, the entire assembly may be manufactured at a cost so low that it may be employed conveniently as a throw-away unit to be discarded after a single application.

In use, the apparatus is stationed adjacent the operating table within easy reach of the operator and close to the patient. Reservoir 20 is filled with heparin or other blood anticoagulant solution. Reservoirs 18 and 20 both are suspended for gravitational flow of their contents. Needle 32 is inserted in the patient's vein in the usual manner.

Conduit 34 is attached to a source of vacuum, for example to a roller pump or to the vacuum line customarily present in the hospital operating room.

As the operation progresses, and blood 12 accumulates in the wound, a member of the surgeon's staff, with bulb-shaped unit 16 held in his hand, places the end of spout 56 in the pool of accumulated blood.

When he wishes to withdraw blood from the wound, he places his thumb or finger over port 37 in which tube 36 terminates. This evacuates blood reservoir 18, with the vacuum being transmitted down through tube 24 into chamber 40 and thence to spout 46. The blood thereupon is sucked up from the pool of blood contained in the wound, transmitted through spout 46, filtered through filter mat 48 for the removal of harmful altered blood components, and passed through tube 24 into reservoir 18 where it builds up a head of blood. The stock of blood thus accumulated may be fed at will back into the circulatory system of the same patient by operation of valve 28 which controls the flow of blood through tube 30 and needle 32.

Control of the rate at which blood is sucked up from the wound is achieved by varying the intensity of the applied suction, or predetermining the size of by-pass tube 36 relative to blood transmittal tube 24. It is a special feature of the system as described and illustrated that filter 48, particularly when wet with blood, acts as a plug preventing the passage of air through the filter as long as thumb opening 37 is open. In other words, as long as the latter situation prevails, conduit 36 will offer the path of least resistance so that air is by-passed to the vacuum line without contacting the collected blood. This is important, because if such contact were present to any great degree it would dry out and cake the blood, and possibly promote its coagulation, with attendant problems.

As the operator withdraws blood from the wound, he meters a predetermined quantity of heparin or other blood anticoagulant solution to both the pool of blood in the wound and the blood collected by the apparatus. This is accomplished by the suction of heparin into the blood upon reducing the pressure in tube 46 supplemented as necessary by pumping the flexible rearward portion of unit 16, containing heparin-filled chamber 42.

With each squeeze, the heparin solution is passed through valve 62 through tube 56, and out ports 64 of head 62. Since ports 64 are directed laterally, the heparin flows not only into the tube, but also out into the pool of blood in which the end of the tube is inserted.

As heparin is discharged through tube 56, a fresh supply is introduced from reservoir 20 into chamber 42 with each relaxing movement of the unit via conduit 24 and associated valve 54. The amount of heparin thus dispensed may be controlled accurately as required to prevent the blood in the suction unit and in reservoir 18 from clotting, without over-heparinizing the patient. This result is achieved by measuring the amount of heparin introduced relative to the amount of blood withdrawn, as for example by calibrating reservoirs 18, 20 and noting the change in fluid levels therein.

Blood intermittently withdawn form the wound is collected in reservoir 18 which accordingly provides a source of the patient's own blood accurately heparinized and freed from harmful components by the action of filter 48. This blood may be returned to the patient gravitationally or by pumping through combination on-off and check valve 28 which controls the flow of blood from reservoir 18 through conduit 30 and needle 32.

The net result is the provision of method and apparatus for autotransfusing blood during surgical procedures which eliminates, or at least sharply reduces, the necessity for the use of blood bank transfusion blood with attendant expense and technical problems.

Having thus described my invention in preferred embodiments, I claim:

1. The method for autotransfusing blood during a surgical procedure involving a bleeding open wound in which blood accumulates in the wound, comprising:
   a. providing conduit means having a first end in communication with the wound and a second end in communication with a blood circulatory member of the patient, said conduit means having a blood storage reservoir intermediate its ends,
   b. intermittently partially evacuating said reservoir to thereby intermittently suck blood from said wound into said first end, through said conduit means, and into said reservoir,
   c. adding a blood anticoagulant to the blood adjacent said first end as the blood is removed from the wound in an amount predetermined to prevent the coagulation of the blood,
   d. promptly filtering the anticoagulant containing blood as it flows though the conduit means to remove harmful components before the blood enters the reservoir,
   e. accumulating the anticoagulant treated and filtered blood in the reservoir below the inlet of the conduit means into said reservoir, whereby the blood is retained in the reservoir without drying,
   f. the evacuation of said reservoir and the addition of said anticoagulant being controlled at a location adjacent the first end of said conduit means,
   g. And returning said reservoir to atmospheric pressure and withdrawing blood from the bottom end of the reservoir and returning it to the circulatory system of the same patient from whom it was collected.

2. The method of claim 1 including the step of adding a blood anticoagulant to the blood in the wound, prior to its collection.

3. Apparatus for autotransfusing blood during surgical procedures involving a bleeding wound in which blood collects in the wound, comprising:
   a. a blood storage reservoir having passageway means at its upper end for communicating said reservoir with a source of vacuum,
   b. first conduit means for interconnecting the wound with the reservoir and second conduit means for interconnecting the reservoir with a blood circulatory member of the patient,
   c. a hand holdable sub-assembly on said first conduit means adjacent the end remote from the reservoir, said sub-assembly comprising: (1.) blood filter means in said conduit means, (2.) dispensing means for dispensing blood anticoagulant into the blood as it is removed from the wound and before it enters the filter means, and (3.) means for controlling communication between said passageway and said source of vacuum;
   d. and blood cycling means in said second conduit means for returning the filtered blood to the circulatory member of the patient.

4. The apparatus of claim 3 wherein the cycling means includes valve means downstream from the reservoir for establishing a controlled gravitational flow of filtered blood through the conduit means and into the circulatory member of the patient.

5. Apparatus for autotransfusing blood during surgical procedures involving an open bleeding wound in which blood accumulates in the wound, the apparatus comprising:
   a. blood conduit means adapted to interconnect the wound and a blood circulatory member of the patient,
   b. intermediate the ends of the conduit means, a reservoir having passageway means at its upper end for communicating the reservoir with a source of vacuum for intermittently partially evacuating the reservoir for intermittently sucking blood into the reservoir from the wound, and
   c. air conduit means communicating at one end operatively with the passageway means and reservoir and terminating at its opposite end adjacent the inlet end of the blood conduit means for selective closing to effect partial evacuation of the reservoir and opening to effect return of the reservoir to atmospheric pressure.

6. Apparatus for autotransfusing blood during surgical procedures involving an open bleeding wound in which blood accumulates in the wound, the apparatus comprising:
   a. a hollow bulb dimensioned to be held in the hand of an operator,
   b. a first chamber in the bulb,
   c. a blood filter in the first chamber,
   d. a suction tube communicating at one end with the upstream end of the first chamber and adapted for placement of its opposite end in a wound,
   e. first conduit means communicating at one end with the downstream end of the first chamber for withdrawing blood therefrom,
   f. a second chamber in the bulb adapted to contain a quantity of liquid blood anticoagulant,
   g. passageway means communicating the second chamber with the suction tube,
   h. valve means in the passageway means for allowing one-way passage of anticoagulant liquid from the second chamber to the suction tube, and
   i. pump means associated with the second chamber for pumping anticoagulant liquid from the second chamber to the suction tube at selected time intervals and in predetermined amount.

7. The apparatus of claim 6 wherein the pump means comprises resiliently deformable side walls of the second chamber for applying manual pumping pressure to the blood anticoagulant liquid contained therein.

8. The apparatus of claim 7 including
   a. a storage vessel for anticoagulant liquid,
   b. an infeed conduit communicating at on end with the storage vessel and at the opposite end with said second chamber, and
   c. valve means associated with the infeed conduit for allowing one-way passageway of anticoagulant liquid from the storage vessel into the second chamber.

9. The apparatus of claim 6 wherein the first conduit means extends through the second chamber and the passageway means extends through the first chamber and terminates adjacent the inlet end of the suction tube.

* * * * *